United States Patent [19]

Imuta et al.

[11] Patent Number: 4,973,703

[45] Date of Patent: Nov. 27, 1990

[54] PROCESS FOR PURIFICATION OF N-CYANO-N'-METHYL-N"-(2-((5-METHYL-IHIMIDAZOL-4-YL)METHYLTHIO)E-THYL)GUANIDINE

[75] Inventors: Junichi Imuta, Ohtake; Noriaki Kihara, Iwakuni; Takeshi Ishitoku, Ohtake, all of Japan

[73] Assignee: Mitsui Petrochemical Industries, Ltd., Tokyo, Japan

[21] Appl. No.: 267,379

[22] Filed: Nov. 4, 1988

[30] Foreign Application Priority Data

Nov. 4, 1987 [JP] Japan .................................. 62-277492

[51] Int. Cl.$^5$ .................. C07D 223/58; C07D 233/64
[52] U.S. Cl. ..................................................... 548/342
[58] Field of Search ......................................... 548/342

[56] References Cited

U.S. PATENT DOCUMENTS 4,381,395  4/1983  Teraji et al. ........................ 548/342

FOREIGN PATENT DOCUMENTS 0031388  7/1981  European Pat. Off. .
0046635  3/1982  European Pat. Off. .
0255376  2/1988  European Pat. Off. .

*Primary Examiner*—John M. Ford
*Assistant Examiner*—Lenora Miltenberger
*Attorney, Agent, or Firm*—Sherman and Shalloway

[57] ABSTRACT

A process for the purification of N-cyano-N'-methyl-N"-[2-{(5-methyl-1H-imidazol-4-yl)methylthio}-ethyl]-guanidine, which comprises bringing a crude product of N-cyano-N'-methyl-N"-[2-{(5-methyl-1H-imidazol-4-yl)-methylthio}ethyl]guanidine into contact with activated carbon in water in the presence of an organic acid.

7 Claims, 1 Drawing Sheet

PROCESS FOR PURIFICATION OF N-CYANO-N'-METHYL-N''-(2-((5-METHYL-IHIMIDAZOL-4-YL)METHYLTHIO)ETHYL)-GUANIDINE

This invention relates to a process for the purification of N-cyano-N'-methyl-N''-[2-{(5-methyl-1H-imidazol-4-yl)methylthio}ethyl]guanidine (to be abbreviated hereinafter as a "cimetidine") useful as a drug, especially as a ulcer treating agent.

Japanese Laid-open Patent Application No. 7172/1984 discloses a process for the production of N-cyano-N'-methyl-N''-[2-{(5-methylimidazol-4-yl)methylthio}ethyl]guanidine by reacting a lower ammonium salt represented by formula N

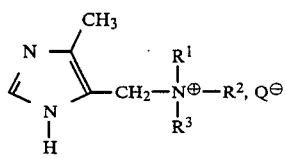

wherein $R^1$, $R^2$ and $R^3$ each denote a lower alkyl group, a lower alkenyl group or an aralkyl group, or $R^1$ and $R^2$, together with the adjacent nitrogen, may form a heterocyclic ring, and Q denotes an acid residue, with N-cyano-N'-methyl-N''-(2-mercaptoethyl)guanidine. In Examples 1-3 thereof, there is described a method in which a purified product is obtained by recrystallization with acetonitrile as a solvent from a crude product containing N-cyano-N'-methyl-N''-[2-{5-methylimidazol-4-yl)methylthio}ethyl)guanidine produced from the corresponding quaternary ammonium salt and the corresponding guanidine.

Japanese Laid-open Patent Application No. 59275/1979 discloses a process for the production of a heterocyclic compound represented by formula

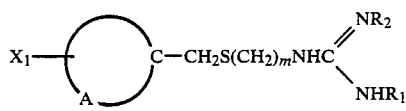

wherein A denotes an imidazole salt group formed together with the carbon atom, $X_1$ denotes a hydrogen atom, a lower alkyl group or a halogen, $R^1$ denotes a hydrogen atom or a lower alkyl group, $R^2$ denotes a hydrogen atom, a nitro group or a cyano group, and m is 2 or 3, by reacting a compound represented by formula

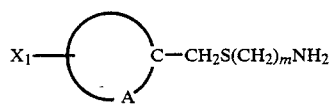

wherein A, $X_1$ and m are as defined above, with a compound represented by formula

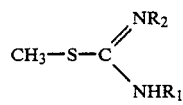

wherein $R^1$ and $R^2$ are as defined above. Example 1 shows a method wherein dilute sulfuric acid and then ethanol are added to the crude product containing 2-[(4-imidazolyl)methylthio]ethylguanidine produced from the corresponding starting compounds according to the aforesaid process, and the resulting product is recrystallized from hydrous ethanol. Example 2 shows that N-[2-{(4-methyl-5-imidazolyl)methylthio}ethyl]-N-nitroguanidine is recrystallized from methanol. Example 3 shows that N-cyano-N'-methyl-N''-[2-{(4-methyl-5-imidazolyl)methylthio}ethyl)guanidine is recrystallized from acetonitrile ether. Example 4 shows that N-cyano-N'-ethyl-N''-[2-{(4-methyl-5-imidazolyl)methylthio}ethyl]guanidine is recrystallized from isopropyl alcohol ether. Example 5 shows that N-cyano-N'-[2-{(4-methyl-5-imidazolyl)methylthio}ethyl]]guanidine is recrystallized from acetonitrile. Example 6 shows that N-cyano-N'-[2-}(4-bromo-5-imidazolyl)methylthio}ethyl]-N''-methylguanidine is recrystallized from nitromethane. Example 7 shows that N-cyano-N'-methyl-N''-3-{(4-methyl-5-imidazolyl)methylthio}propyl]-guanidine is recrystallized from isopropyl alcohol ether. Example 8 shows that N-cyano-N'-methyl-N''-[2-(4-imidazolylmethylthio)ethyl)guanidine is recrystallized from acetonitrile.

Japanese Laid-open Patent Application No. 100372/1979 discloses a process for the production of 4-methyl-5-chloromethylimidazole hydrochloride by reacting 4-methylimidazole with formaldehyde or an oligomer of formaldehyde in an aqueous solution in the presence of excess hydrogen chloride at a temperature of 25° to 160° C. Examples 1 and 2 show a method wherein 4-methyl-5-chloromethylimidazole hydrochloride produced according to the aforesaid process is separated from the reaction mixture as a precipitate by filtration, washed with a HCl-containing ether (further with an ether in Example 2) and dried in vacuo.

Japanese Laid-open Patent Application No. 105664/1985 is a parent application of the divisional application, Japanese Laid-open Patent Application No. 59275/1979, having the same Examples as disclosed in the divisional application.

The purification methods described in the aforesaid laid-open official gazettes thus show that the imidazole derivatives resulting from the reaction are purified in free form as such or as mineral acid salts (sulfuric acid salts or hydrochloric acid salts).

Japanese Patent Publication No. 24422/1978 discloses a process for the production of a compound represented by formula

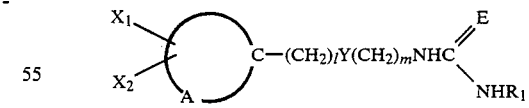

wherein
$X_1$ and $X_2$ each denote H, lower alkyl, OH, benzyl, halogen, amino or

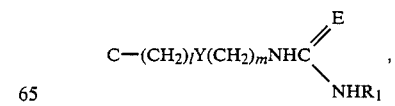

or $X_1$ and $X_2$ may form a ring together with at least two atoms constituting an A ring, A denotes an unsaturated heterocyclic group formed together with the carbon atom and containing at least one nitrogen atom and which may contain the other hetero atom, Y denotes oxygen, sulfur or NH, l and m each denote an integer of 0 to 4 and the sum of l and m is 3, E denotes oxygen or sulfur, and $R_1$ denotes lower alkyl, acyl or dialkylaminoalkyl, by reacting a compound represented by formula

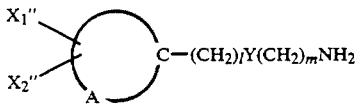

wherein $X_1''$ and $X_2''$ are the same or different and each denote H, lower alkyl, OH, benzyl, halogen, amino or $(CH_2) Y(CH_2)_m NH_2$ or $X_1''$ and $X_2''$ may form a ring together with at least two atoms constituting an A ring, and A, l, m and Y are as defined above, with a compound represented by formula

wherein $R_1$ and E are as defined above.

Japanese Patent Publication No. 24422/1978 thus involves a process for producing urea or thiourea derivatives as is apparent from the definition for E in the above formula. (C) in Example 1 thereof shows a method wherein 4(5)-((2-aminoethyl)thiomethyl)imidazole corresponding to the starting amino compound (a compound represented by formula including $X_1''$ and $X_2''$) is produced by the reaction of cysteamine hydrochloride with 4(5)chloromethylimidazole hydrochloride in the presence of sodium ethoxide, and reacted with picric acid to form its dipicrate.

Japanese Laid-open Patent Application No. 129550/1985 discloses a compound represented by formula,

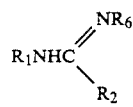

wherein $R_1$ denotes a group of formula Het$-$($CH_2$)$-$S$-$($CH_2$)$_n$ in which Het denotes a 5- or 6-membered nitrogen-containing heterocyclic ring such as imidazole, pyridine, thiazole, isothiazole, thiadiazole, isoxazole or triazole, which may be substituted by lower alkyl, hydroxyl, halogen or amino, and n is 2 or 3, $R_2$ denotes lower alkyl, phenyl, phenyl substituted with hydroxyl or mercapto, $SR_4$ or $NHR_5$ in case $R_3$ is other than hydrogen, $R_6$ is hydrogen, lower alkyl or $R_1$, $R_4$ and $R_5$ each denote lower alkyl, and $R_6$, together with $R_4$ or $R_5$, may form a 5-membered ring such as thiazoline or imidazoline, and a process for producing same.

Example 6 thereof shows production of N,N'-bis-[2-{5-methyl-4-imidazolyl)methylthio}ethyl]acetamidine trihydrochloride via tripicrate of the same acetamidine. Example 7 shows production of 2-[2-{(5-methyl-4-imidazolyl)methylthio}ethyl]amino-2-imidazoline dihydrochloride via picrate of the same imidazoline. Example 10 shows production of N,N'-bis-[2-{(5-methyl-4-imidazolyl)methylthio}ethyl]-N'-methylguanidine via its tripicrate.

However, cimetidine having a sufficient purity can hardly be obtained by the aforesaid processes.

It is known that cimetidine can be present crystallographically in the form of many polymorphs. Japanese Patent Publication No. 22967/87 discloses polymorphs called cimetidines A, B and C. It describes that cimetidine A can be formed with good reproducibility by correctly selecting a crystallization catalyst and carefully controlling stirring of a solvent just before and during crystallization.

It is an object of this invention to provide a novel process for the purification of cimetidine, i.e. a process for the production of highly pure cimetidine.

Another object of this invention is to provide a process for the production of highly pure cimetidine in varied crystal forms.

The other objects and advantages of this invention will be made clear from the following explanation.

This invention can achieve such objects and advantages by a process for the purification of N-cyano-N'-methyl-N''-[2-{5-methyl-1H-imidazol-4-yl)methylthio}ethyl]guanidine, which comprises bringing a crude product of N-cyano-N'-methyl-N''-[2-{(5-methyl-1H-imidazol-4-yl)methylthio} ethyl]guanidine into contact with activated carbon in water in the presence of an organic acid.

Figure 1:
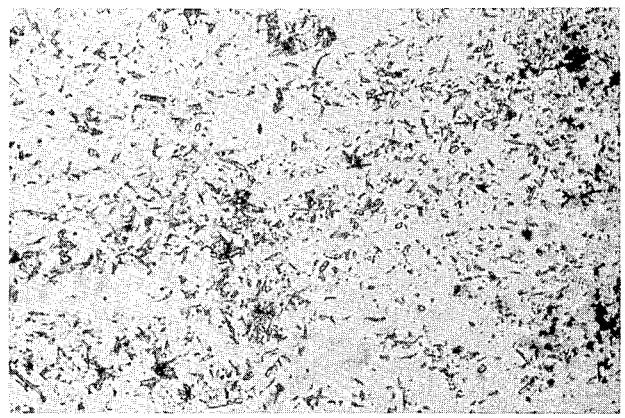
FIG. 1 is a photomicrograph (150× magnification) of cimetidine crystals (Run No. 8) obtained by a process described in Example 2 of this invention.
Figure 2:
FIG. 2 is a photomicrograph showing a crystal structure of a comparison mixture obtained by mechanically mixing 59% of cimetidine polymorph A with 41 % of cimetidine polymorph B.

What this invention terms N-cyano-N'-methyl-N''-[2-{(5-methyl-1H-imidazol-4-yl)methylthio}ethyl)]guanidine is a compound represented by formula (I):

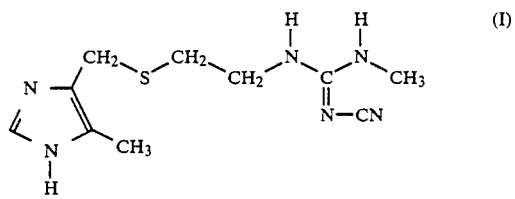

The crude product of the imidazole derivative represented by formula (I) can be formed by varied methods. For example, a method for producing cimetidine from inexpensive starting materials such as ammonia and formaldehyde via N-cyano-N'-methyl-N''-[2-butane-2,3-dionyl)thioethyl]guanidine is disclosed in British Patent No. 2025969, Spanish Patent No. 455991 and Japanese Laid-open Patent Application No. 92257/1985. These methods are applied to the production of the crude product of the imidazole derivative represented by formula (I).

A method for the production of cimetidine by reacting N-cyano-N'-methyl-N''-[2-(butane-2,3-dionyl)thioethyl]guanidine with a carboxylic acid ammonium salt or formaldehyde and a method for the production of the other imidazole derivatives of formula (I) according to the above method are also employable which were proposed before by Applicant of this application.

That is, the imidazole derivative of formula (I) can be produced by the reaction of N-cyano-N'-lower alkyl-N''-[2-(butane-2,3-dionyl)thioethyl]guanidine with a carboxylic acid ammonium salt and a lower aliphatic aldehyde such as formaldehyde or acetaldehyde.

Preferable examples of the carboxylic acid ammonium salt used in the above methods are ammonium salts of monocarboxylic acids containing 1 to 8 carbon atoms such as ammonium formate, ammonium acetate, ammonium monochloroacetate, ammonium dichloroacetate, ammonium trichloroacetate, ammonium methoxyacetate, ammonium propionate, ammonium butyrate, ammonium isobutyrate and ammonium benzoate.

Preferable examples of the reaction solvent used in the above methods are alcohols such as methanol, ethanol, propanol, isopropanol and butanol; ethers such as diethyl ether, diisopropyl ether, tetrahydrofuran and dioxane; esters such as methyl acetate and ethyl acetate; nitriles such as acetonitrile and propionitrile; and amides such as formamide and N,N-dimethylformamide.

A molar ratio of the carboxylic ammonium salt to said guanidine is 2 to 20, preferably 3 to 15. A molar ratio of aldehyde to said guanidine is 1 to 10, preferably 1.2 to 5.

The weight of the solvent is usually 1 to 18 times, preferably 5 to 70 times that of said guanidine.

The reaction temperature is usually $-10°$ to 150° C., preferably 15° to 120° C. The reaction time varies with the reaction temperature and other conditions, and is usually 0.2 to 50 hours, preferably 0.3 to 40 hours.

The process of this invention is carried out by bringing the resulting crude product into contact with activated carbon in water in the presence of an organic acid regardless of the method for the production of the imidazole derivative represented by formula (I).

The acid used in this invention is an organic acid, and a carboxylic acid is preferably used as an organic acid. Aliphatic carboxylic acids, above all, saturated aliphatic carboxylic acids having 1 to 4 carbon atoms are preferable as an organic carboxylic acid. Examples of such carboxylic acids are formic acid, acetic acid, propionic acid, n-butyric acid and isobutyric acid. Among these acids, acetic acid is advantageously used.

In this invention, the organic acid is used in an amount of preferably 1 to 100 mols, more preferably 1 to 20 mols per mol of cimetidine in the crude product being purified.

Examples of activated carbon can be those of various origins which may be in various forms such as powder, granules, etc.

Activated carbon is used in a proportion of 0.01 to 100 parts by weight, preferably 0.1 to 100 parts by weight per part by weight of the cimetidine crude product being treated.

A temperature at which to bring the cimetidine crude product into contact with activated carbon in water in the presence of the organic acid is preferably 0° to 150° C., more preferably 10° to 80° C.

The contact time is preferably 0.1 to 50 hours, more preferably 0.5 to 10 hours.

The concentration in water of the cimetidine crude product is usually 0.5 to 50 g/100 cc, preferably 2 to 30 g/100 cc, more preferably 5 to 20 g/100 cc.

The process of this invention is performed by, for example, a method in which activated carbon is added to an aqueous solution comprising a cimetidine crude product, an organic acid and water and the mixture is treated under stirring, a method in which the aqueous solution is passed through a column filled with activated carbon, or a method comprising a combination of these methods with time. In the above method, stirring can be carried out for e.g. 0.1 to 50 hours, preferably 0.5 to 10 hours.

From the aqueous solution treated with activated carbon, the activated carbon is then separated by filtration, and the residue is then neutralized with an alkaline aqueous solution to precipitate crystals. The resulting crystals are water-washed and dried to give purified cimetidine white crystals.

Study of the present inventors reveals that cimetidine can easily be obtained in varied crystal forms to meet varied needs by subjecting the purified cimetidine white crystals formed in accordance with the process of this invention to the following treatment.

Namely, the cimetidine white crystals are dissolved in an alcohol or a lower alkyl nitrile or an aqueous solution of the alcohol or the lower alkyl nitrile. With mechanical stirring at a given stirring rate, e.g. 5 to 700 rpm, cooling starts at a given cooling rate, e.g. 10° to 80° C./hr from a reflux temperature. After given amounts of seed crystals, i.e. 0.01 to 10 % by weight of the seed crystals based on cimetidine are added at a given temperature, e.g. 10° to 60° C., the temperature is lowered to a given final temperature, e.g. 0° to 30° C. and cimetidine is then precipitated. Examples of the alcohol used on this occasion are methanol, ethanol, n-propanol and isopropanol. Among these, isopropanol is preferable. Examples of the lower alkylnitrile are acetonitrile and propionitrile. Acetonitrile is preferable. A water content of an aqueous solvent of the alcohol or the lower alkylnitrile is 1 to 30% by volume, preferably 1 to 10% by volume. After stirring continues at the given final temperature for a while, the crystals are filtered off and dried to obtain purified cimetidine.

Cimetidine is known to have many polymorphs. In the above method, when using a nonaqueous solvent, a cimetidine polymorph A is 100% obtained; in using an aqueous solvent, a mixture of cimetidine polymorths A and B at a ratio of 96:4 to 18:82 can optionally be obtained by changing the precipitation conditions such as the temperature in adding seed crystals, amounts of the seed crystals and a stirring rate.

The following Referential Example and Examples illustrate this invention more specifically.

REFERENTIAL EXAMPLE (Production of crude cimetidine)

A mixture of 2.42 g of N-cyano-N'-methyl-N''-[2-butane-2,3-dionylthio)ethyl]guanidine, 0.8 g of paraformaldehyde, 3.1 g of ammonium acetate and 25.4 ml of isopropanol was reacted at 50° C. for 3 hours. After the reaction was over, the solvent was distilled off, and the residue was dissolved in water and neutralized with 5N sodium hydroxide. The precipitated crystals were filtered off, water-washed and dried to obtain cimetidine as pale yellow crystals. Twenty milligrams of the crystals were taken out and dissolved in 0.4 ml of methanol, and two microliters of the solution was subjected to thin layer chromatography (TLC) of silica gel. Using a TLC scanner (CS-930: a tradename for a machine manufactured by Shimazu Seisakusho), reflective absorption at 400 nm was measured and the integral value was found to be 2395. TLC was conducted in 10 cm with a solvent mixture of ethyl acetate/acetone/water (5/4/1) as an eluent. The TLC plate was dried and reflective absorption at 225 nm was analyzed with the TLC scanner. Purity of cimetidine was then found to be 92.7%.

EXAMPLE 1

Two grams of crude cimetidine having purity of 92.7%, which was obtained as in Referential Example, was added to a solution of 0.95 g of acetic acid and 20 g of water, and stirred at room temperature and dissolved. Activated carbon (0.4 g) was added and the mixture was further stirred at room temperature for 1 hour. Activated carbon was separated by filtration, and the filtrate was washed with 2 ml of water. The filtrate and the washing were put together, and neutralized with 4 g of 5N sodium hydroxide aqueous solution. Crystals were filtered off, washed with 4 ml of water and dried to obtain 1.55 g (recovery ratio 78%) of cimetidine white crystals. Twenty milligrams of said crystals were taken out and dissolved in 0.4 milliliter of methanol, and subjected to TLC as in Referential Example to analyze reflective absorption at 400 mn. The integral value was then found to be 0. As in Referential Example, after the development, reflective absorption at 225 nm was analyzed. Purity of the resulting cimetidine was then found to be 96.7%.

Three grams of the cimetidine white crystals obtained in the process of this invention were added to 90 ml of isopropanol (IPA), and they were mechanically stirred at 85° C. and 300 rpm for 10 minutes to form a uniform solution. The temperature of the solution was lowered at a cooling rate of 30° C./hr, and when 45° C. was reached, 1 mg of seed crystals were added. The temperature was lowered to 25° C. and stirring further continued for 30 minutes. Subsequently, crystals were filtered off and dried. There resulted 2.7 g (recovery ratio 90%) of white crystals of cimetidine polymorph A.

EXAMPLES 2-10

Two grams of crude cimetidine having purity of 92.7%, which was obtained as in Referential Example, was added to a solution of 0.95 g of acetic acid and 20 g of water, and stirred at room temperature and dissolved. Activated carbon (0.4 g) was added and stirring further continued at room temperature for 1 hour. Activated carbon was separated by filtration and the filtrate was washed with 2 ml of water. The filtrate and the washing were put together, and neutralized with 4 g of 5N sodium hydroxide aqueous solution Crystals were filtered off, washed with 4 ml of water and dried to afford 1.55 g (recovery ratio 78%, purity 97.0%) of cimetidine white crystals.

Three grams of the cimetidine white crystals obtained in the process of this invention were added to 12 ml of a solution of IPA and $H_2O$ at a ratio of 95:5, and they were mechanically stirred at 85° C. and 300 rpm or 500 rpm for 10 minutes to form a uniform solution. The temperature of the solution was decreased at a given precipitation rate of 30° C./hr or 50° C./hr. When 45° C. was reached, 15 mg, 6 mg or 1 mg of cimetidine polymorph B was added as seed crystals When the temperature was lowered to 25° C., stirring continued for 30 minutes. Thereafter, crystals were filtered off and dried to give cimetidine white crystals containing polymorphs A and B. A mixing ratio of polymorphs A and B was found by preparing a calibration curve from a ratio of absorbances in characteristic absorption at 1205 $cm^{-1}$ of polymorph A and characteristic absorption at 1180 $cm^{-1}$ of polymorph B in IR spectrum. The results of measurement under varied conditions are shown in Tables 1, 2 and 3.

TABLE 1

Influence of temperatures in adding seed crystals

| Example | Temperature in addition of seed crystals (°C.) | Recovery ratio (%) | Crystal form (%) | Melting point (°C.) |
|---|---|---|---|---|
| 2 | 35 | 79 | A24–B76 | 139.8–141.8 |
| 3 | 45 | 70 | A18–B82 | 140.1–141.4 |

Conditions:
Amounts of seed crystals: 15 mg
Cooling rate: 50° C./hr
Stirring rate: 300 rpm

TABLE 2

Influence of amounts of seed crystals

| Example | Amounts of seed crystals (mg) | Stirring rate (rpm) | Cooling rate (°C./hr) | Recovery ratio (%) | Crystal form (%) | Melting point (°C.) |
|---|---|---|---|---|---|---|
| 2 | 3 | 500 | 50 | 70 | A96–B4 | 140.3–141.5 |
| 5 | 6 | " | " | 72 | A65–B35 | 140.0–142.0 |
| 3 | 15 | " | " | 70 | A18–B82 | 140.1–141.4 |

Condition:
Temperature in adding seed crystals: 45° C.

TABLE 3

Influence of stirring rate

| Example | Amounts of seed crystals (mg) | Stirring rate (rpm) | Cooling rate (°C./hr) | Recovery ratio (%) | Crystal form (%) | Melting point (°C.) |
|---|---|---|---|---|---|---|
| 6 | 3 | 50 | 300 | 74 | A85–B15 | 140.1–142.0 |
| 7 | " | " | 500 | 70 | A78–B22 | 139.8–141.6 |
| 8 | " | 30 | 300 | 79 | A59–B41 | 139.5–141.4 |
| 9 | 1 | " | " | 69 | A93–B7 | 140.3–142.0 |
| 10 | " | " | 500 | 77 | A80–B20 | 140.1–142.2 |

Condition:
Temperature in adding seed crystals: 45° C.

What we claim is:

1. A process for the purification of N-cyano-N'-methyl-N''-[2-{(5-methyl-1H-imidazol-4-yl)methylthio}ethyl]guanidine, which comprises bringing a crude product of N-cyano-N'-methyl-N''-[2-{(5-methyl-1H-imidazol-4-yl)methylthio}ethyl]guanidine into contact with activated carbon in water in the presence of an organic acid.

2. The process of claim 1 wherein the organic acid is an organic carboxylic acid.

3. The process of claim 1 wherein the organic acid is an aliphatic carboxylic acid.

4. The process of claim 1 wherein the organic acid is used in a proportion of 1 to 100 mols per mol of N-cyano-N'-methyl-N''-[2-{(5-methyl-1H-imidazol-4-yl)methylthio}ethyl]guanidine.

5. The process of claim 1 wherein the activated carbon is used in a proportion of 0.01 to 100 parts by weight per part by weight of N-cyano-N'-methyl-N''-[2-{(5-methyl-1H-imidazol-4-yl)methylthio}ethyl]guanidine.

6. The process of claim 1 wherein the contact is carried out at a temperature of 0° to 150° C.

7. The process of claim 1 wherein the contact time is 0.1 to 50 hours.

* * * * *